(12) United States Patent
Yang et al.

(10) Patent No.: US 8,148,600 B2
(45) Date of Patent: Apr. 3, 2012

(54) IMMUNOCOMPROMISED RODENTS AS DUAL COLOR TUMOR MODELS

(75) Inventors: Meng Yang, San Diego, CA (US); Eligio Reynoso, San Diego, CA (US); Mingxu Xu, San Diego, CA (US); Ping Jiang, San Diego, CA (US)

(73) Assignee: Anticancer, Inc., San Diego, CA (US)

( * ) Notice: Subject to any disclaimer, the term of this patent is extended or adjusted under 35 U.S.C. 154(b) by 580 days.

(21) Appl. No.: 10/775,554

(22) Filed: Feb. 9, 2004

(65) Prior Publication Data

US 2004/0231013 A1 Nov. 18, 2004

Related U.S. Application Data

(60) Provisional application No. 60/445,583, filed on Feb. 7, 2003.

(51) Int. Cl.
*A01K 67/027* (2006.01)
*A01K 67/02* (2006.01)

(52) U.S. Cl. ................ 800/18; 800/13; 800/22

(58) Field of Classification Search .......... 800/18, 800/13, 22
See application file for complete search history.

(56) References Cited

U.S. PATENT DOCUMENTS

| | | | |
|---|---|---|---|
| 6,251,384 | B1 | 6/2001 | Tan et al. |
| 6,759,038 | B2 | 7/2004 | Tan et al. |
| 2002/0026649 | A1 | 2/2002 | Tan et al. |
| 2003/0088883 | A1 | 5/2003 | Breindl et al. |

FOREIGN PATENT DOCUMENTS

| | | |
|---|---|---|
| WO | WO-02/28188 | 4/2002 |
| WO | WO 02/28188 A1 * | 4/2002 |

OTHER PUBLICATIONS

Okabe et al. (1997) FEBS Lett., vol. 467, 313-319.*
Yang et al. (2002) PNAS, vol. 99(6), 3824-3829.*
Verkhusha et al. (2001) J. Biol. Chem., vol. 276(32), 29621-29624.*
Amsterdam, A., et al., Dev. Biol. (1995) 171:123-129.
Chalfie, M., et al., Science (1994) 263:802-805.
Delagrave, S., et al., BioTechnology (1995) 13:151-154.
Heim, R., et al., Proc. Natl. Acad. Sci. USA (1994) 91:12501-12504.
Hu, W., FEBS Lett. (1995) 369:331-334.
Ikawa, M., FEBS Lett. (1995) 375:125-128.
Ikawa, M., Dev. Growth Diff. (1995) 37:455-459.
Niwa, H., Gene (1991) 108:193-199.
Okabe, et al., FEBS Lett. (1997) 407:313-319.
Peters, K.G., et al., Dev. Biol. (1995) 171:252-257.
Sheen, J., et al., Plant J. (1995) 8:777-784.
Wang, S., et al., Nature (1994) 369:400-403.
Yang, M., et al., Proc. Natl. Acad. Sci. USA (2003) 100:14259-14262 (Nov. 25 issue).
International Search Report for PCT/US04/03636, mailed on Jan. 5, 2005, 3 pages.
Yang et al., PNAS (2002) 99(6):3824-3829.
Hoffman, Cell Death and Differentiation (2002) 9(8):786-789.
Hoffman, Lancet Oncology (2002) 3(9):546-556.
Supplementary European Search Report for EP 04709430.5, mailed on Jun. 9, 2006, 3 pages.
Brown et al., Nature Medicine (2001) 7(7):864-868.
Fukumura et al., Cell (1998) 94:715-725.
Office Action for European Patent Application No. EP 04 709 430.5, mailed on Jun. 18, 2008, 6 pages.

* cited by examiner

*Primary Examiner* — Anne Marie S Wehbe
(74) *Attorney, Agent, or Firm* — Morrison & Foerster LLP

(57) ABSTRACT

Immunocompromised rodents that have been modified to express a fluorescent protein in substantially all tissues are described. These rodents are useful as models for gene expression, tumor progression and angiogenesis. Also provided are model systems where heterologous tissues fluorescing in a first color are transplanted into hosts that have been modified to fluoresce in substantially all tissues with a second color.

6 Claims, 3 Drawing Sheets

TRANSGENIC GFP NUDE MOUSE

IMMUNOCOMPROMISED RODENTS AS DUAL COLOR TUMOR MODELS

CROSS-REFERENCE TO RELATED APPLICATIONS

This application claims benefit of U.S. provisional application 60/445,583 filed 7 Feb. 2003. The contents of this document are incorporated herein by reference.

TECHNICAL FIELD

This application relates to the production and use of transgenic immunocompromised rodents including athymic nude mice that visibly express fluorescent protein in multiple tissues while maintaining their immunocompromised state. The rodents may be used for whole body optical imaging of cells and tissues, including the visualization of tumors and metastases present in said rodents, in particular, tumors provided fluorescent proteins of alternative emission spectra.

BACKGROUND ART

Fluorescent proteins that emit light in the presence of stimulating radiation in the absence of substrate have been used as research tools for many years. The best known and initially used such protein is the green fluorescent protein (GFP) isolated from a *Aequorea victoria*, but a large number of such proteins have been isolated from other sources or obtained synthetically which display a wide variety of emission maxima so that the historical term GFP has been used to describe proteins that appear in a full spectrum of visible color, including red, blue, and yellow. See, e.g., Delagrave, S., et al., *BioTechnology* (1995) 13:151-154; Heim, R., et al., *Proc. Natl. Acad. Sci. USA* (1994) 91:12501-12504. A number of organisms have been successfully modified to express such fluorescent proteins. These include *Caenorhabditis elegans* (Chalfie, M., et al., *Science* (1994) 263:802-805), *Drosophila melanogaster* (Wang, S., et al., *Nature* (1994) 369:400-403), zebrafish (Peters, K. G., et al., *Dev. Biol.* (1995) 171:252-257; Amsterdam, A., et al., *Dev. Biol.* (1995) 171:123-129), *Dictyostelium* and *Arabidopsis thaliana* (Sheen, J., et al., *Plant J.* (1995) 8:777-784; Hu, W., *FEBS Lett.* (1995) 369:331-334).

Okabe, et al., *FEBS Lett.* (1997) 407:313-319, have inserted the wild-type GFP into pCAGGS (containing the chicken beta-actin promoter and cytomegalovirus enhancer, beta-actin intron and bovine globin polyadenylation signal—Niwa, H., *Gene* (1991) 108:193-199) and produced transgenic mouse lines (Ikawa, M., *FEBS Lett.* (1995) 375:125-128; and Ikawa, M., *Dev. Growth Diff.* (1995) 37:455-459). Although a bright green light emission was observed in the muscle and pancreas of more than 20 of these transgenic mouse lines, GFP expression was not ubiquitous and light emission was not visible to the naked eye in other tissues. However, when a modified form (EGFP) was used in this expression system, the transgenic mice express the EGFP transgene in the entire body, from pre-implantation embryo to adult stages.

Wild-type eggs fertilized with green male sperm were not green at the 2-cell stage but subsequently became green after subsequent stages of embryogenesis. Newborns were green fluorescent. The blood vessels were classified as 'bright' in the EGFP-bearing lines. The hair of these animals was not green. Transgenic mice were uniformly green with the exception of hair and red blood cells. The brain, liver, kidney, adrenal gland and testis, lung, muscle, heart, intestine, and adipose tissue, thymus, spleen and testicular cells fluoresced green when irradiated with blue excitation light.

The transgenic mouse lines were normal despite a significant amount of EGFP expression; EGFP therefore is non-toxic.

One embodiment of the immunocompromised rodents exhibiting fluorescence described in the invention is reported in Yang, M., et al., *Proc. Natl. Acad. Sci. USA* (2003) 100: 14259-14262 (November 25th issue).

Citation of documents herein is not intended as an admission that any is pertinent prior art. All statements as to the date or representation as to the contents of documents is based on the information available to the applicant and does not constitute any admission as to the correctness of the dates or contents of the documents.

DISCLOSURE OF THE INVENTION

For reasons that are not clear, transgenic immunocompromised rodents, such as athymic nu/nu mice are rare. The present invention provides for the production of fluorescent proteins in such immunocompromised rodents. The resulting rodents are useful for the imaging of cells and tissues in vivo, in particular as recipients of transplanted cells or tissues, such as tumors, which can be observed against the background of GFP expressing cells and tissues of the transgenic rodents. Thus, the transplanted cells or tissues express visible indicator, such as, but not limited to, another fluorescent protein. The transplanted cells or tissues may be observed by contrast against the background of GFP expressing cells and tissues of the transgenic rodents of the invention. The transplanted cells or tissues may comprise tumor cells or cells that are otherwise cancerous such that their growth properties and/or spread may be monitored.

The transgenic immunocompromised rodents may also be used to screen for the effect of various agents on interactions between the host rodent tissue and the transplanted cell or tissue. Examples of such agents include drugs or candidate drugs to modulate host-transplant interactions or modulate growth and spread of transplanted cells or tissue.

The rodents may also be used as a source of GFP expressing cells or tissues for further study and/or transplantation into another animal or embryo. Optionally, such transplantation is serial in nature, and may be used to study aging as one embodiment. The transplanted cells may include embryonic and adult stem cells.

In one embodiment, the GFP expressing rodents are athymic nu/nu mice obtained by first crossing a GFP expressing mouse with nu/nu mice. The F1 generation is then collected and crossed with each other to produce progeny including GFP expressing nu/nu mice. Male and female GFP expressing nu/nu mice from the F1×F1 cross are then used to produce GFP expressing nu/nu mice progeny. These resultant mice may be crossed with nu/nu non-GFP expressing nu/nu mice to maintain GFP expressing nu/nu mice.

Similar strategies are used to obtain other immunocompromised rodents, such as immunocompromised rats where immunocompromised strains are crossed with normal strains that have been modified to express fluorescent protein.

Thus, in one aspect, the invention is directed an immunocompromised transgenic rodent that expresses a first fluorescent protein in essentially all tissues while maintaining its immunocompromised phenotype. In a further embodiment, the invention is directed to this rodent transplanted with heterologous tissue, said tissue modified to express a second fluorescent protein with a different emission spectrum from the first fluorescent protein. In another aspect, the invention is directed to a transgenic rodent that expresses a gene encoding a first fluorescent protein in essentially all tissues and which has been transplanted by heterologous tissue that expresses a second fluorescent protein having a different emission spectrum from said first fluorescent protein.

In still another aspect, the invention is directed to a method to assay the effects of a drug on tumor host interactions by contacting a rodent that expresses a first fluorescent protein and which harbors tumor cells expressing a second fluorescent protein of a different color comprising contacting said rodent with a drug or protocol and observing the effects on the tumor cells contained in the host.

MODES OF CARRYING OUT THE INVENTION

Figure 1:
FIG. 1 is a whole body image of orthotopically growing human colon cancer after implantation into an immunocompromised mouse. The tumor expresses red fluorescent protein, while the host exhibits whole body expression of fluorescent protein that emits green light.

The invention relates to GFP expressing immunocompromised rodents such as athymic nu/nu mice as well as to methods for the preparation and use thereof. The rodents express GFP in essentially all tissues, preferably at levels such that light emission is visible to the naked eye. The rodents are otherwise immunocompromised—e.g., athymic nu/nu mice, and may be used, for example, as hosts to accept transplants of human tumor tissue or other xenografts.

Using similar techniques to those described herein, other immunocompromised rodents, such as rats, expressing GFP can be obtained.

The term "GFP" may be used for convenience as an acronym not only for fluorescent proteins that appear green, but in general for fluorescent proteins of any color that are capable of emitting light in response to incident exciting radiation. It will be clear from the context whether GFP is used in the generic sense or is used to designate a protein that actually admits green fluorescent light.

As used herein, "GFP" refers to a fluorescent protein of whatever wavelength emitted as well as "enhanced" forms of GFP and the *Aequorea Victoria* green fluorescent protein. The description of transplanted cells or tissues labeled with a visible indicator, such as fluorescent dyes and as generally known in the art, is selected such that a different color fluorescent protein is used in the transplanted cells or tissues in comparison to the fluorescent protein expressed in the host. As a non-limiting example, if green GFP is expressed in the transgenic rodents of the invention, then the transplanted cells or tissues may express red fluorescent protein (RFP).

Moreover, and in the case of transplanting multiple cells or tissues, labeling with different colors is provided by the instant invention to permit the cells or tissues to be visualized and/or followed simultaneously. Non-limiting examples of other fluorescent colors include yellow, blue, and far-red. The expression of other fluorescent indicators may optionally be specific to individual cell types, genes or processes. Non-limiting examples of how to provide such specificity include by operably linking sequences encoding the fluorescent indicators to be under the regulatory control of a promoter that is cell specific, a promoter that is responsive to particular activation events, a promoter that regulates the expression of a particular gene of interest, and a promoter that regulates the expression of a gene product involved in a cell process of interest.

The immunocompromised rodents may also be used as a source of cells and/or tissues that express GFP. Non-limiting examples of such tissues include an embryo or embryo tissues; stem cells, and cells or tissues of the brain, liver, kidney, adrenal gland, testis (including testicular cells), lung, muscle, heart, intestine, ovary and spleen as well as adipose tissue.

The transplantation of tissues modified to contain fluorescent protein with a different emission spectrum from that of the host can be practiced to a limited extent with immunocompetent subjects as well. In order to practice this aspect of the invention in immunocompetent subjects, the transplanted tissue must be syngeneic or the observations must be limited to short term exploration of an immune response or other response, including rejection of the transplant.

Turning again to the transgenic, GFP-expressing, immunocompromised rodents of the invention, these may be used to visualize gene expression in the manner taught by Yang, et al. ("Visualizing Gene Expression by Whole-Body Fluorescence Imaging." *Proc. Natl. Acad. Sci. USA* (2000) 97:12278-12282), which describes visualization, by noninvasive techniques, transgene expression in intact animals. That system permits rapid visualization of transgene expression in major organs of intact live mice which is simple, rapid, and eminently affordable. Against the background of the GFP transgenic, a fluorescent protein of different color is expressed in the cells such as those of brain, liver, pancreas, prostate, and bone, and its fluorescence is encoded in whole-body optical images. As non-limiting examples, higher-magnification imaging may be performed with a trans-illuminated epifluorescence dissecting microscope while low-magnification imaging may be performed atop a fluorescence light box and directly viewed with a thermoelectrically cooled color charge-coupled device camera, or using simpler LED-based devices.

The fluorescent transgenic rodents may be provided with the expression system to be tested by directly injecting expressible vector-borne nucleic acid encoding fluorescent protein (such as, but not limited to $8 \times 10^{10}$ plaque-forming units/ml of adenoviral expression system encoding fluorescent protein in 20-100 µl PBS and 10% glycerol) into a tissue such as the brain, liver, pancreas, prostate, or bone marrow. Within 5-8 h after injection, the fluorescence of the expressed GFP in tissues like the brain becomes visible, and whole-body images are recorded at video rates. The GFP fluorescence continues to increase for at least 12 h and remains detectable in tissues like the liver for up to 4 months. Real-time recordings may be made without requiring either exogenous contrast agents (where the vector encoded GFP is not the same as the GFP expressed in rodent tissues), radioactive substrates, or long processing times. This method requires only that the expressed coding sequence or promoter to be tested be fused or operatively linked to the vector borne GFP to allow the study of the therapeutic and diagnostic potential of suitably tagged genes in relatively opaque organisms or, as here, in fluorescent rodents.

In another aspect, transgenic rodents may also be imaged and used in the manner taught by Yang, et al. ("Whole-Body Optical Imaging of Green Fluorescent Protein-Expressing Tumors and Metastases," *Proc. Natl. Acad. Sci. USA* (2000)

97:1206-1211) which describes a whole-body optical imaging system. Such a system affords unprecedented continuous visual monitoring of cell growth and spread, including that exhibited by transplanted (and optionally cancerous) cells or tissues, in this case labeled with expressed GFP of a different hue within intact animals.

In preferred embodiments of the invention, the fluorescent rodents contain transplanted fluorescent tumors growing and metastasizing in the live rodents. Non-limiting examples of such tumors include human and rodent tumors that stably express very high levels of a GFP as described by Yang, et al. (supra). Tumors that express a GFP other than the GFP expressed in the rodent host are used. As indicated above, the immunocompromised fluorescent rodents of the invention are preferred for this method resulting in dual labeling of the host that can be maintained over long periods of time; however, for short-term studies or studies using syngeneic tumors, such as rodent tumors transplanted into rodents, even immunocompetent transgenic fluorescent rodents may be used.

As a non-limiting example, B16F0-GFP mouse melanoma cells are injected into the tail vein or portal vein of 6-week-old fluorescent immunocompromised rodents. Whole-body optical images are used to show metastatic lesions such as those that may develop in the brain, liver, and bone. The B16F0-GFP cells are readily visualized to provide real time, quantitative measurement of tumor growth in each of these organs.

In another non-limiting example, AC3488-GFP human colon cancer may be surgically implanted orthotopically. Whole-body optical images may be used to show, in real time, growth of the primary colon tumor and its metastatic lesions in the liver and skeleton.

The invention also provides for methods of using the fluorescent, immunocompromised rodents to identify, or screen for, modulators of cancer growth. In one embodiment, the methods may be used to identify inhibition by potential chemotherapeutic agents. Thus, the model of tumor progression in the fluorescent immunocompromised rodents of the invention is established by implantation, preferably orthotopically, of cancer cells or intact portions of a tumor that expresses a fluorescent protein with an emission of different wavelength from that of the background provided by the transgenic host. Once the model is established, the candidate chemotherapeutic agents or protocols are administered to the host and the effect on tumor progression and metastasis is directly observed.

Immunocompromised fluorescent rodents may also be used to image angiogenesis in the manner taught by Yang, et al. ("Whole-Body and Intravital Optical Imaging of Angiogenesis in Orthotopically Implanted Tumors," *Proc. Natl. Acad. Sci. USA* (2001) 98:2616-2621). The instant invention thus also provides for methods of assaying for tumor-induced vascularization. These methods are an adaptation of the orthotopic implantation model for angiogenesis measurement by using tumors labeled with a GFP for grafting into fluorescent rodents. The use of a GFP emitting a different color from that of the host GFP-expressing capillaries of the host to be clearly visible against the tumor fluorescence as examined either intravitally or by whole-body luminance in real time. This is preferably practiced with human tumors to permit intravital images of orthotopically implanted human pancreatic tumors to show angiogenic capillaries at both primary and metastatic sites, in the immunocompromised labeled hosts of the invention. A quantitative time course of angiogenesis may be determined for an orthotopically growing human prostate tumor periodically imaged intravitally in a single rodent over a 19-day period.

Whole-body optical imaging of tumor angiogenesis may be demonstrated, for example, by injecting fluorescent Lewis lung carcinoma cells into the subcutaneous site of the footpad. The footpad is relatively transparent, with comparatively few resident blood vessels, and thus allows quantitative imaging of tumor angiogenesis (such as by increases in capillary density) in the intact animal.

In an alternative embodiment, the GFP expressing human breast tumor MDA-MB-435 may be orthotopically transplanted to the fat pad which is then imaged to detect changes, particularly increases, in blood vessel density linearly over an extended period, such as up to or beyond 20-week period. Such powerful and clinically relevant angiogenesis nude mouse models may also be used for real-time in vivo evaluation of agents inhibiting or promoting tumor angiogenesis in physiological microenvironments, as described above, by observing the effect of the agent on angiogenesis.

In yet another aspect, the rodents of the invention may be used in a manner analogous to that described by Yang, et al. ("Direct External Imaging of Nascent Cancer, Tumor Progression, Angiogenesis, and Metastasis on Internal Organs in the Fluorescent Orthotopic Model," *Proc. Natl. Acad. Sci. USA* (2002) 99:3824-3829) to overcome limits on the sensitivity of external imaging due to light scattering by intervening tissue, most especially skin. The invention thus provides for opening a skin-flap in the light path to markedly reduce signal attenuation and increase detection sensitivity manyfold. The observable depth of tissue is greatly increased and many tumors that were previously hidden become clearly observable.

The skin flap can be reversibly opened and closed. Typically, after anesthetizing the animal, an arc-shaped incision is made in the skin and subcutaneous connective tissue is separated to free the skin flap. The flap can be closed by suturing. The invention thus provides for observations made on the internal organs of a tumor model system.

The ability to observe, directly through the opened skin flap, the labeled tumor cells greatly enhances the sensitivity and resolution of the model system of the invention. The model can be used simply to monitor the progress of the condition or can be used as a means to evaluate potential therapeutics, as well as to evaluate effects which may result in more negative outcomes than no treatment at all. In this instance, a compound and/or protocol is supplied to test animals and compared to controls where the compound and/or protocol are not present. Enhancement of tumor progression, angiogenesis and/or metastasis in the presence of these experimental conditions indicates that the compound and/or protocol is deleterious to the subject; similarly, inhibition of any of these features identifies the compound and/or protocol as a potential therapeutic.

In one embodiment, single tumor cells, expressing fluorescent protein, are seeded on the brain image through a scalp skin-flap. Lung tumor microfoci representing a few cells are viewed through a skin-flap over the chest wall, while contralateral micrometastases are imaged through the corresponding skin-flap. Pancreatic tumors and their angiogenic microvessels are imaged by means of a peritoneal wall skin-flap. A skin-flap over the liver allows imaging of physiologically relevant micrometastases originating in an orthotopically implanted tumor. Single tumor cells on the liver arising from intraportal injection are also detectable. Cells or tissues expressing two different GFP's, such as host tissues versus transplanted tissues or two transplanted tissues, may also be visualized by the use of a skin flap. Particularly preferred is the use of a lower-abdominal skin-flap to visualize tissues of the prostate or the surrounding area.

Methods for providing cells or tissues for transplant with a GFP are known. Tumor cells may be provided with an expression system for one or more fluorescent proteins using standard methods. The cells may be transduced in vitro and grown into tumors in vitro or in vivo and the resulting tumors transplanted in to the model subject. The cells may be injected or may be transplanted surgically. Surgical orthotopic transplantation is preferred when a model of tumor progression is desired. However, other methods of providing the model with modified tumor cells that stably express the fluorescent protein may also be used. In addition, rodents of the invention that bear an endogenous tumor or introduced tumor may be provided with a viral vector, particularly a retroviral vector, for expression of a GFP protein of emission different from that of the host by infecting the tumor already present in the animal. This is especially relevant with respect to models for tumor-susceptible mammals such as the "oncomouse" described in U.S. Pat. No. 4,736,866. This vector is preferably introduced locally and directly to the already present tumor.

Generally, any model of tumor progression, angiogenesis, and/or metastasis which relies for observation on the emission of fluorescence may be used with fluorescent rodents and methods of the invention.

In many instances, a single color is used to observe the metastasis of a single tumor. However, the method of the invention includes simultaneous observation of two or more tumors each labeled with a different color of fluorescent protein. By utilizing this method, not only is it possible to obtain multiple observations of multiple tumor progressions, the effects or interferences of each tumor on the other can be observed directly.

The methods of the invention have a number of advantages. First, enhanced sensitivity permits observation of only a single or two transplanted cells against a background of fluorescent host cells and tissues. Second, angiogenesis is directly observable, which is extremely important in evaluating therapeutic efficacy of proposed compounds and protocols. Third, it is possible to observe multiple transplanted tissues (such as tumors) simultaneously. This is especially important because of the phenomenon of interference between disparate tissues or tumors. Since multiple different colors can be used, the interaction of separate tissues or tumors can be observed directly. Fourth, because it is possible to make observations over substantial periods of time in the immunocompromised fluorescent rodents, distinctions can be made between cells that are actively proliferating and dormant cells. Thus, the presence of dormant cells can be determined by the method of the invention.

In a further aspect, the fluorescent hosts may be injected with detectable, preferably visible, compounds for generating images against the GFP background of the nude mouse tissues. As a non-limiting example, a visible indicator, such as a dye, may be injected into the bloodstream of a mouse of the invention to visualize all or part of the circulatory system. This is particularly appropriate where the red blood cells of the rodent do not express visible GFP, leaving the bloodstream without detectable light emissions.

The following examples are provided to illustrate the invention and are not limiting.

Example 1

Production of GFP Expressing Nude Mice

C-57 B6-GFP mice (Okabe, M., et al., *FEBS Lett* (1997) 467:313-319) were crossed with nu/nu mice. The C-57/B6-GFP mice were obtained from the Research Institute for Microbial Diseases at Osaka University. These mice expressed *A. Victoria* GFP under control of the chicken beta-actin promoter and CMV enhancer. All tissues except erythrocytes and hair fluoresced green under excitation light.

The F1 generation was collected and crossed with each other. Two rare GFP nu/nu mice, one male and one female, were obtained. The GFP nu/nu male and GFP nu/nu female were crossed with each other and produced a litter of 6 GFP nu/nu mice.

Figure 3:
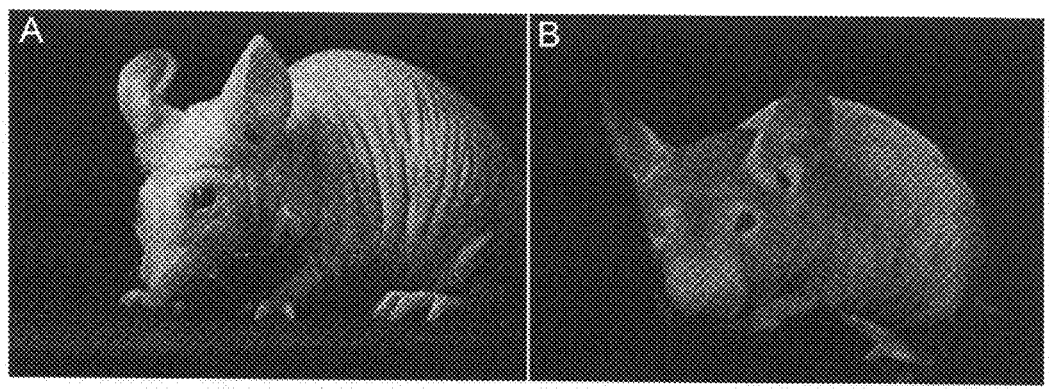
FIG. 3 shows the transgenic mouse of the invention in contrast to a non-transgenic nude mouse.

A male GFP nu/nu mouse was crossed with a female nu/nu non-GFP mouse. Nine nude nu/nu offspring were produced. All expressed fluorescence in the tissues generally. See FIG. 3, which contrasts non-GFP nu/nu to GFP nu/nu mice.

Example 2

Preparation of Tumors With Red Fluorescent Protein

Red fluorescent protein (RFP), DsRed2 (Clontech) was inserted into $pLNCX_2$ (Clontech) at the EgII and NotI sites.

Saturating amounts of the resulting vector, $pLNCX_2$-DsRed2 were incubated for 18 h with a precipitated mixture of DOTAP reagent (Boehringer Mannheim) and PT67 packaging cells at 70% confluence. PT67 cells are an NIH 3T3-derived packaging cell line expressing the 10 A1 viral envelope, and were cultured in DMEM (Irvine Scientific) supplemented with 10% heat-inactivated FBS. Fresh medium was replenished at this time, and cells were examined by fluorescence microscopy 48 h posttransfection. For selection of brightly fluorescing cells producing high-titer retroviral supernatants, the RFP-expressing packaging cells were cultured in the presence of 500-2,000 μg/ml G418 increased in a stepwise manner (Life Technologies, Grand Island, N.Y.) for 7 days.

Desired tumor cell lines at 20% confluence were incubated with a 1:1 precipitated mixture of retroviral supernatants of PT67 cells and RPMI 1640 or other culture media (GIBCO) containing 10% FBS (Gemini Biological Products) for 72 h. Fresh medium was replenished at this time. Tumor cells were harvested with trypsin/EDTA and subcultured at a ratio of 1:15 into selective medium, which contained 50 μg/ml G418. To select brightly fluorescent cells, the level of G418 was increased to 800 μg/ml in a stepwise manner. Clones expressing RFP were isolated with cloning cylinders (Bel-Art Products) by trypsin/EDTA and were amplified and transferred by conventional culture methods in the absence of selective agent.

The tumor cells which were thus obtained as red fluorescent cells included:
- rodent B16F0 melanoma cells;
- mouse MMT060562 mammary tumor cells;
- mouse Dunning prostate carcinoma cells;
- human PC-3 prostate carcinoma cells; and
- human HCT-116 colon cancer cells.

Example 3

Dual-Labeled Model of Tumor Progression

HCT-116-RFP—i.e., human colon cancer cells labeled with red fluorescent protein, were harvested by trypsinization, washed three times with cold serum-free medium and re-suspended with serum-free RPMI medium 1640. The cells were injected within 40 minutes of harvesting into 6-week-old transgenic female GFP nude mice, as prepared in Example 1, by exposure of the colon through a lower-left abdominal incision. $10^6$ HCT-116-RFP cells in 50 μl were injected under the serosa of the descending colon using a 25 μl syringe. The incision in the abdominal wall was closed with a 6-0 surgical suture in one layer. The animals were kept under ketamine anesthesia during surgery.

Whole-body imaging was performed in a fluorescent light box illuminated by fiber-optic lighting at 470 nm (Lightools Research, Encinitas, Calif.). Emitted fluorescence was collected through a long-pass filter GG475 (Chroma Technology, Brattleboro, Vt.) on a Hamamatsu C5810 three-chip cooled color CCD camera (Hamamatsu Photonics, Bridgewater, N.J.) High-resolution images of 1,024/724 pixels were captured directly on an IBM PC, Images were processed for contrast and brightness and analyzed with the use of Image Pro Plus 3.1 software (Media Cybernetics, Silver Spring, Md.).

FIG. 1 shows a whole-body image of the orthotopically growing HCT-116-RFP human colon cancer 10 weeks after the implantation. The image was acquired in a fluorescent light box with a CCD camera. As shown, this system readily distinguishes tumor from the host.

Example 4

Interaction of Macrophages with Prostate Tumor

PC-3-RFP, i.e., human prostate cancer cells labeled with red fluorescent protein were harvested by trypsinization, washed 3 times with cold serum-containing medium, and kept on ice. Within 40 minutes, $10^6$ cells in 30 μl were injected into bladder and prostate of the immunocompromised mice obtained in Example 1 as follows: Bladder and prostate were exposed after a lower midline abdominal incision; after injection, the incision was closed with a 6-0 surgical suture, and the animals kept under isoflurane anesthesia.

For observation, fresh tissue was cut into approximately 1 mm³ pieces and pressed on slides for fluorescence microscopy. In the microscopic visualization, an Olympus BH 2-RFCA fluorescence microscope equipped with a mercury 100-W lamp power supply was used to visualize both GFP and RFP fluorescence at the same time. Excitation light was produced through a D425/60 bind pass filter, 470 DCXR dichroic mirror. Emitted fluorescence light was collected through a long pass filter GG475 (Chroma Technology). High-resolution images of 1,024/724 pixels were captured by a Hamamatsu C5810 three-chip cooled color CCR camera (Hamamatsu Photonics) and directly stored on an IBM PC. Images were processed for contrast and brightness and analyzed with the use of Image Pro Plus 4.0 software (Media Cybernetics).

Figure 2:
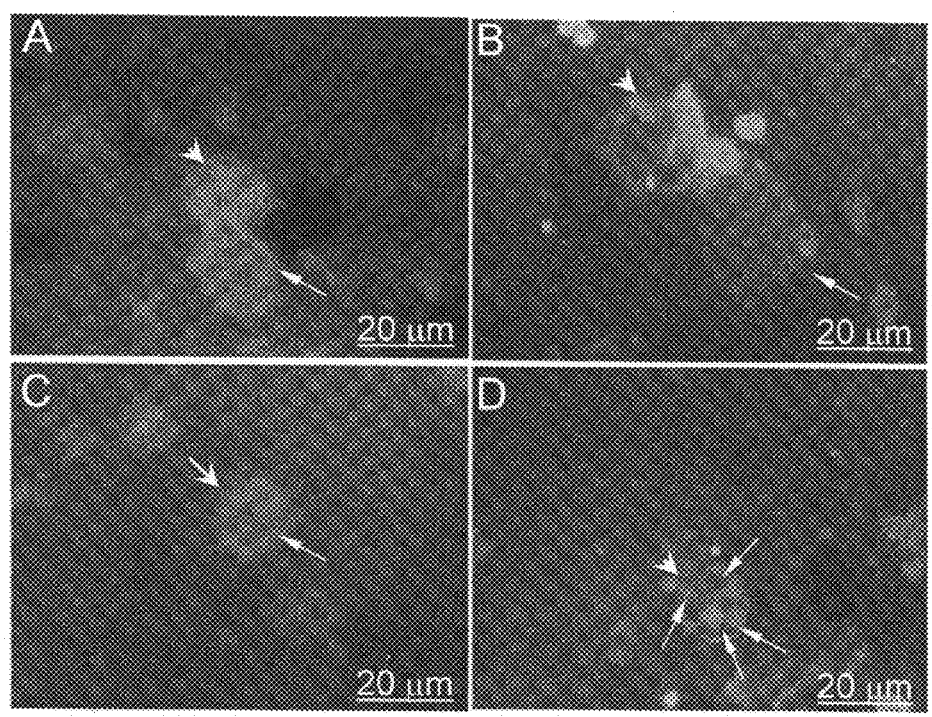
FIGS. 2A-2D show real-time interaction of macrophages in the immunocompromised host that are labeled with green fluorescent protein wherein the cancer cells are labeled with red fluorescence. The figure shows initial contact (FIG. 2A), engulfment (2B), the cancer cell engulfed in the macrophage (2C), and the cancer cell digested by the macrophage (2D).

The interaction of macrophages, which fluoresce green by virtue of the transgenic nude mouse, are shown interacting with the tumor cells in FIG. 2. This picture was taken 35 days after implantation. Panel A shows host GFP macrophage contacting RFP cancer cells; Panel B shows the GFP macrophage engulfing the RFP cancer cell; Panel C shows an RFP cancer cell engulfed by the GFP macrophage and Panel D shows the ultimate digestion of the RFP cancer cell by macrophage.

Example 5

Studies in Fluorescent Immunocompetent Mice

Short term studies using dual-color imaging can be conducted on immunocompetent subjects when syngeneic transplants are employed. In the murine model described by Okabe, C57/B6-GFP mice were produced. Studies were conducted with $10^6$ RFP expressing mouse B16F0 melanoma cells, $10^6$ RFP-expressing mouse MMT060562 mammary tumor cells and $10^6$ RFP-expressing Dunning (rat) prostate cancer cells. Using these techniques, angiogenesis in live tumor tissue could be observed 3 weeks after injection of B16F10-RFP melanoma cells and interaction of host dendritic cells and tumor cells in fresh tumor tissue was observed as well. Lymphocyte infiltration was observed with the breast cancer model Thus, dual-color images of early events in tumor angiogenesis could be observed as well as interactions of the immune system with the transplanted tumor.

The invention claimed is:

1. An immunocompromised transgenic rodent which is heterozygous for expression of a first fluorescent protein in all tissues except hair and erythrocytes and maintains an immunocompromised phenotype,
    wherein said transgenic rodent is further modified to contain a tumor that expresses a second fluorescent protein that emits a wavelength different from that of the first fluorescent protein, and
    wherein said tumor grows in said transgenic rodent for at least 10 weeks.
2. The rodent of claim 1 which is a mouse.
3. The mouse of claim 2 which is a nu/nu mouse.
4. The rodent of claim 1 which is prepared by a process which comprises
    first, crossing a rodent that expresses said first fluorescent protein by virtue of derivation from a fertilized egg provided with a transgenic expression system comprising a nucleotide sequence encoding said first fluorescent protein operatively linked to a promoter that effects said expression in all said tissues, which rodent is not immunocompromised
    with a rodent that does not express the fluorescent protein and is immunocompromised to produce F1 offspring,
    second, crossing those F1 offspring that express said first fluorescent protein in all tissues except hair and erythrocytes to obtain F2 offspring that express said first fluorescent protein and are immunocompromised;
    third, crossing those F2 offspring that express said first fluorescent protein in all tissues except hair and erythrocytes and are immunocompromised with a rodent that does not express said first fluorescent protein and is immunocompromised to obtain F3 offspring that are heterozygous for said expression of said first fluorescent protein and are immunocompromised;
    modifying said F3 offspring to contain a tumor that expresses a second fluorescent protein that emits a wavelength different from that of the first fluorescent protein, thus producing rodents of claim 1.
5. The rodent of claim 4 which is a mouse.
6. The mouse of claim 5 which is a nu/nu mouse.

* * * * *